Figure 1:
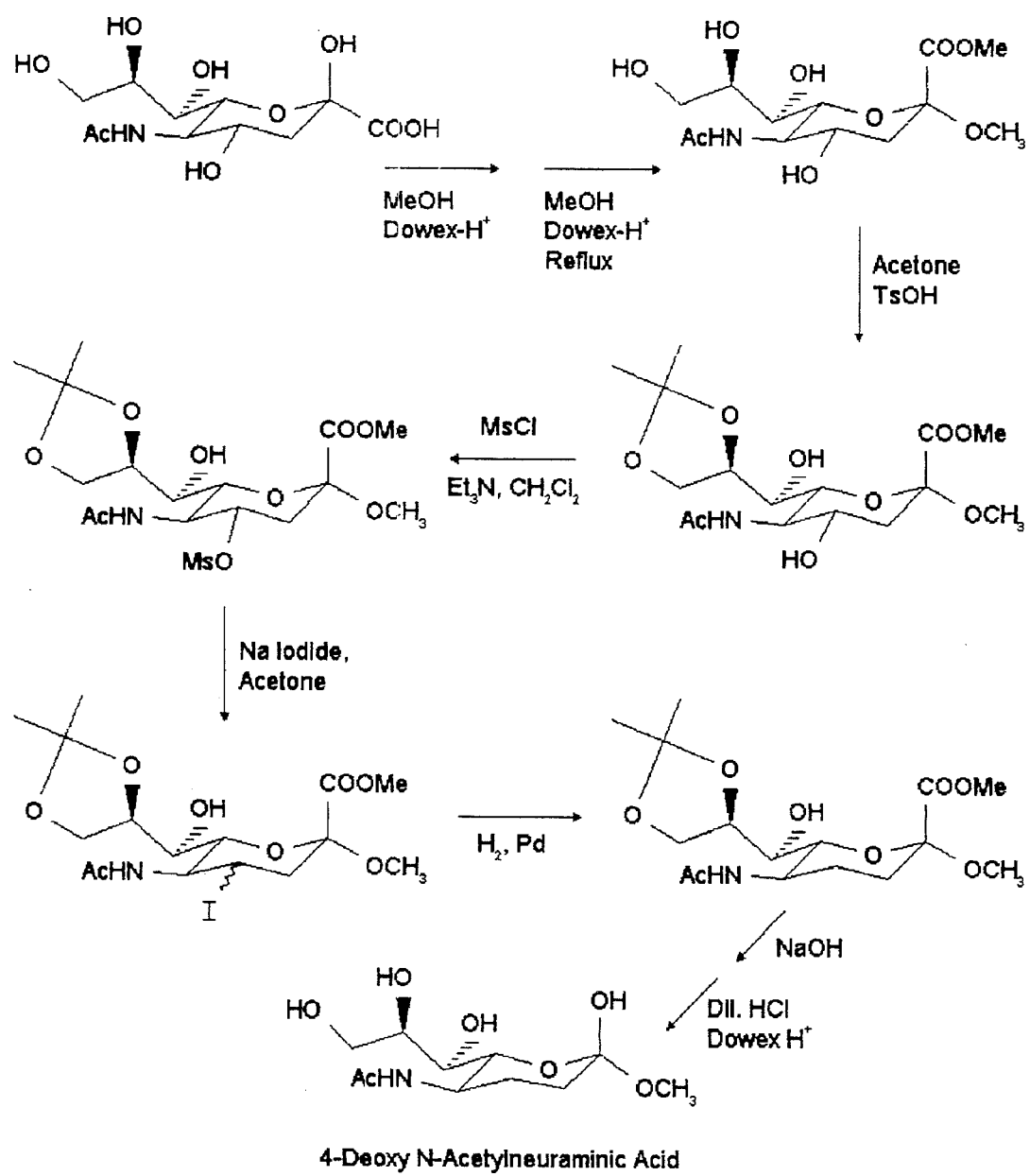

United States Patent [19]

Turner et al.

[11] Patent Number: 5,663,055

[45] Date of Patent: Sep. 2, 1997

[54] METHODS FOR DIAGNOSING HUMAN INFLUENZA AND 4-POSITION MODIFIED CHROMOGENIC N-ACETYLNEURAMINIC ACID SUBSTRATED FOR USE THEREIN

[75] Inventors: Gregory A. Turner, Independence, Mo.; James F. Maher, Broken Arrow, Okla.; C. Worth Clinkscales, Tulsa, Okla.; Michael D. Roark, Owasso, Okla.

[73] Assignee: Oklahoma Medical Research Foundation, Oklahoma City, Okla.

[21] Appl. No.: 354,914

[22] Filed: Dec. 13, 1994

Related U.S. Application Data

[63] Continuation-in-part of Ser. No. 254,653, Jun. 3, 1994, abandoned, which is a continuation of Ser. No. 866,186, filed as PCT/US90/07681, Dec. 27, 1990, abandoned, which is a continuation-in-part of Ser. No. 458,805, Dec. 29, 1989, abandoned.

[51] Int. Cl.$^6$ .............................. C12Q 1/34; C12Q 1/70; C12N 9/26
[52] U.S. Cl. ........................... 435/18; 435/5; 435/84; 435/201; 536/18.4
[58] Field of Search ..................... 536/4.1, 17.2, 536/18.4; 435/5, 18, 84, 201

[56] References Cited

U.S. PATENT DOCUMENTS

| | | | |
|---|---|---|---|
| 3,950,322 | 4/1976 | Thomas et al. | 260/234 |
| 4,772,553 | 9/1988 | Fujii et al. | 435/13 |
| 4,810,636 | 3/1989 | Corey | 435/14 |
| 5,252,458 | 10/1993 | Liav et al. | 435/18 |
| 5,556,963 | 9/1996 | Liav et al. | 536/55.3 |

OTHER PUBLICATIONS

Kiyotani et al. "Fluorometric Measurement of Neuraminidase Activity of Influenza Virus", Hiroshima Journal of Medical Sciences, vol. 33, No. 2 (1984) pp. 287–292.

Journal of Infectious Disease, vol. 142, No. 4, issue 1980, Yolken et al. "Fluorometric assay for Measurement of Viral Neuraminidase–Application to the Rapid Detection of Virus in Nasal Wash Specimens", pp. 516–523 (see abstract).

Biological Abstracts, vol. 82, No. 12, issued 1987, Takei et al., "Enzymologically different characteristics between influenza A and B virus neuraminidases," abstract No. 117445: Virus (Tokyo) 36(1) 119–124 (1986): see abstract.

Biological Abstracts, vol. 79, No. 3, issued 1985, Kiyotani et al., "Fluorometric measurement of neuraminidase activity of influenza viruses," abstract No. 27461; Hiroshima, J. Med. Sci. 33 (2): 287–292 (1984), see abstract.

Gross et al., Biochemistry (1988) 27:4279–4283.

Kim et al., Journal American Chemical Society (1988) 110(19):6481–6486.

Kiyotani et al., Microbiol. Immunol. (1987) 31(11):1131–1135.

Kiyotani et al., Zbl. Bakt. Hyg. A (1985) 260:173–285.

Myers et al., Analytical Biochemistry (1980) 101:166–174.

Pachucki et al., Journal of Clinical Microbiology (1988) 26(12):2664–2666.

Santer et al., Biochimica et Biophysica Acta (1978) 523:435–442.

Yolken et al., Reviews of Infectious Diseases (1982) 4(1):35–68.

Yolken et al., Clinical Chemistry (1981) 27(9):1490–1498.

Zbiral et al., Liebigs. Ann. Chem. (1989) pp. 519–526.

Zbiral et al., Monatshelfte für Chemie (1988) 119:127–141.

Baumberger et al., Helvetica Chimica Acta (1986) 69(8):1927–1935.

Hagedorn et al., Helvetica Chimica Acts (1986) 69(8):2127–2133.

Baumberger et al., Hevetica Chimica Acta (1986) 69(7):1535–1541.

Beau et al., European Journal of Biochemistry (1980) 106(2):531–540.

Gross et al., Glycoconjugate Journal (1987) 4(2):145–156.

Primary Examiner—Ralph Gitomer
Attorney, Agent, or Firm—Fitch, Even, Tabin & Flannery

[57] ABSTRACT

Chromogenic derivatives of N-acetylneuraminic acid modified in the 4-position to contain a hydrogen atom, a fluorine atom, a methoxy group, or an ethoxy group are used as substrates in colorimetric assays for human influenza neuraminidase activity in clinical specimens for the purpose of selectively diagnosing influenza infection. The substrates may exhibit different reactivity with the different types of influenza neuraminidases, thus enabling one to discern the specific type of influenza infection and prescribe appropriate treatment and/or supportive therapy therefor.

31 Claims, 7 Drawing Sheets

2-[4-Nitrophenyl]-4-Deoxy-N-Acetylneuraminic Acid
-alpha-ketoside (sodium salt)

METHODS FOR DIAGNOSING HUMAN INFLUENZA AND 4-POSITION MODIFIED CHROMOGENIC N-ACETYLNEURAMINIC ACID SUBSTRATED FOR USE THEREIN

RELATED APPLICATIONS

This application is a continuation-in-part of U.S. patent application Ser. No. 08/254,653, filed on Jun. 3, 1994 now abandoned; which was a continuation of U.S. patent application Ser. No. 07/866,186; filed Aug. 24, 1993, now abandoned; which was a continuation-in-part of U.S. application Ser. No. 07/458,805, filed Dec. 29, 1989, now abandoned. This application is also related to PCT Application PCT/US90/07681, filed on Dec. 27, 1990, which was based on U.S. application Ser. No. 07/458,805, filed Dec. 29, 1989.

TECHNICAL FIELD

The present invention relates to diagnostic tests for human influenza. More specifically it relates to chromogenic substrates that are useful in the diagnosis of influenza through the detection of the enzymatic activity of human influenza neuraminidase (NA).

BACKGROUND OF THE INVENTION

Influenza virus averages 30–50 million infections annually in the United States alone. Epidemiologic studies of influenza epidemics estimate the incidence of infection to be 25% in the general population and higher in school age children. Researchers have estimated that up to half the infected persons would see a physician because of the illness. In 1986, the Center for Disease Control (CDC) estimated that influenza epidemics have been associated with 10,000 or more excess deaths in 18 of the preceding 28 years. CDC studies indicate influenza as the fifth leading cause of death in the United States. Antigenic variations in the surface glycoproteins of influenza A and B and reassortment of viral proteins in influenza A account for their continued epidemics.

Influenza viruses possess surface glycoproteins that have NA activity. These glycoproteins are members of a family of neuraminidases that are found in viruses, bacteria, mycoplasmas, and animal tissues. They hydrolyze substrates that contain alpha-ketosidically linked N-acetylneuraminic acid (Neu5Ac; referred to previously as "NANA"). In viruses, NA typically constitutes 5–10% of the viral protein and exists as a mushroom-shaped spike on the envelope. Viral NA is composed of a hydrophilic area which includes the catalytic site of the enzyme and a hydrophobic area that is inserted into the viral envelope anchoring the enzyme to the virus.

Various assays for NA activity are described in the literature. Santer, U. V., et al., Biochimica et Biophysica Acta 523:435–442 (1978), describes a colorimetric assay for NA using 2-(3-methoxyphenyl)-N-acetyl-alpha-D neuraminic acid as a substrate and 4-aminoantipyrine in the presence of an oxidizing agent to measure the enzymatically released methoxyphenol. Myers, R. W., et al., Analytical Biochemistry 101:166–174 (1980), describes the use of the 4-methylumbelliferyl-alpha-ketoside of Neu5Ac in a fluorometric assay for NA. This fluorogenic derivative of Neu5Ac was also used in studies of the NA activity of influenza viruses by Yolken, R. H., et al., J. Infectious Diseases 142:5116–523 (1980); Clinical Chemistry 27:1490–1498 (1981); and Reviews of Infectious Diseases 4:35–68 (1982); and by Kiyotani et al., Hiroshima J. Medical Sciences 33:287–292 (1984); Zbl Bakt Hyg A260-273–285 (1985); Microbiol. Immun. 31:1131–1135 (1987). Despite the availability of these prior NA assays, however, physicians currently still diagnose influenza solely on the basis of symptomology. This is in part due to the fact that these prior assays were complicated and/or required equipment not typically found in a clinical setting. Another shortcoming of these prior assays is that they were unable to discriminate between influenza type. That ability is particularly important to enable physicians to prescribe the appropriate chemotherapy and/or supportive therapy to combat the infection.

Prior workers have investigated the relationship between the chemical structure of Neu5Ac and its biological function as a substrate for non-influenza NA. Gross, H. J. et al., Biochemistry 27:4279 (1988), examined benzyl-alpha-glycosides of N-acetyl-4-epi-D-neuraminic acid as a substrate for three different bacterial NAs (C. perfringens, A. ureafaciens, and V. cholera) and found significant differences in reactivity. After 22 hours, the C. perfringens NA cleaved 100% of the substrate while the A. ureafaciens and V. cholera NAs cleaved only 50% and 11% of the substrate, respectively. Kim et al., J. Am. Chem. Soc. 110:6481–6486 (1988) described the structural characteristics of substrates accepted by Neu5Ac aldolase, its use in the synthesis of Neu5Ac, and its chemical conversion to the 2-deoxy derivatives, and additionally reported that work was in progress to determine the biological activity of the 2-deoxy derivatives. Brossmer et al., Helv. Chim. Acta 69:2127 (1986); Glycoconjugates 4:145 (1987) reported that the methyl-alpha-glycoside of 4-deoxy Neu5Ac was a good substrate for fowl plague viral Neu5Ac, but not for the three bacterial NAs mentioned above. Additionally, Schauer, R., et al., Eur. J. Biochem. 106:531 (1980), reported that 4-methoxy Neu5Ac was an excellent substrate for fowl plague viral NA but not for V. cholera NA. The 4-methylumbelliferyl derivative of 4-deoxy Neu5Ac is also described in the literature (Helv. Chim. Acta. 69:1927 (1986)). Zbiral et al., Monatsheft fur Chemie 119:127–141 (1988) described the synthesis of 7- and 8-deoxy Neu5Ac and 4,7-dideoxy Neu5Ac. Zbiral et al., Liebigs Ann. Chem. 119:127–141 (1989) described the synthesis of the 4-methylumbelliferyl-2-α glycosides of 7-epi, 8-epi, 7,8-bis-epi, 8-deoxy, 9-deoxy and 4,7-dideoxy Neu5Ac and investigated the behavior of those compounds as inhibitors of the sialidase from V. cholera.

Applicant is unaware of any prior reports on the reactivity of 4-modified Neu5Acs with human influenza NA.

SUMMARY OF THE INVENTION

The 4-modified Neu5Ac substrates useful in the present invention are of the following general formula:

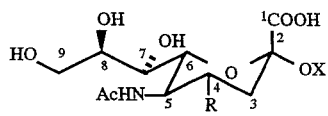

where Ac represents acetyl, R represents hydrogen, fluorine, methoxy, or ethoxy, and X represents a chromogenic group that exhibits distinct color when cleaved from the substrate or a salt of the substrate. The above general formula also illustrates the numbering system used for the 5-NeuAc substrates. These chromogenic substrates are useful in methods, tests, and kits for the diagnosis of influenza through the detection of the enzymatic activity of human influenza neuraminidase.

One aspect of the invention is a method of detecting human influenza neuraminidase activity in a clinical sample suspected of having such activity, said method comprising:

(a) incubating the clinical sample with a chromogenic modified N-acetylneuraminic acid substrate of the formula:

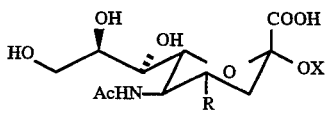

where Ac represents acetyl, R represents hydrogen, fluorine, methoxy, or ethoxy and X represents a chromogenic group that exhibits a distinct color when cleaved from the substrate or a salt of the substrate by the human influenza neuraminidase activity; and (b) detecting human influenza neuraminidase activity by observing whether the incubated clinical sample exhibits the distinct color after step (a).

Another aspect of the invention is a method of selectively detecting a specific type (e.g., A or B) of human influenza neuraminidase activity in a clinical sample suspected of having human influenza neuraminidase activity, said method comprising:

(a) incubating the clinical sample with a chromogenic modified N-acetylneuraminic acid substrate of the formula:

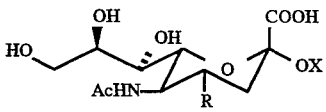

where Ac represents acetyl, R represents hydrogen, fluorine, methoxy, or ethoxy, and X represents a chromogenic group that exhibits a distinct color when cleaved from the substrate or a salt of the substrate by the specific type of human influenza neuraminidase activity;

(b) observing the color exhibited by the incubated clinical sample after step (a); and (c) comparing the color exhibited by the incubated clinical sample to colors exhibited by standards of the specific type of human influenza neuraminidase activity and other types of human influenza neuraminidase activity with the substrate.

Yet another aspect of the invention is a modified Neu5Ac chromogenic substrate useful for detecting human influenza neuraminidase activity in a clinical sample suspected of having such activity, said substrate having the formula:

where Ac represents acetyl, R is methoxy, ethoxy, or fluorine, and X is a chromogenic group that exhibits a distinct color when cleaved from the substrate and salts of the substrate by the human influenza neuraminidase activity.

Still another aspect of the invention is a chromogenic substrate useful for detecting human influenza neuraminidase activity in a clinical sample suspected of having such activity, said substrate having the formula:

where Ac represents acetyl, R is hydrogen, and X is a chromogenic group selected from the group consisting of 3-cyanoumbelliferyl, 2- or 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethyl-aminophenyl, 4-chloro-1-naphthyl, and 6-bromo-2-naphthyl and salts of said substrate.

These and other objects or aspects of the invention will be apparent from a consideration of the specification.

BRIEF DESCRIPTION OF THE DRAWINGS

FIG. 1 is a schematic diagram depicting the synthesis procedure described in Example 1.

FIG. 2 is a schematic diagram depicting the synthesis procedure described in Example 2.

FIG. 3 is a schematic diagram depicting the synthesis procedure described in Example 3.

FIG. 4 is a schematic diagram depicting the synthesis procedure described in Example 4.

FIG. 5 is a schematic diagram depicting the synthesis procedure described in Example 5.

FIG. 6 is a schematic diagram depicting the synthesis procedure described in Example 6.

FIG. 7 is a comparison of 4-modified and non-modified N acetyl neuraminic acid substrates in the detection of naturally-occurring mammalian sialidase. Similar sialidase may be present in both healthy and influenza-positive individuals. The comparison is described in more detail in Example 9.

DETAILED DESCRIPTION OF THE INVENTION

The chromogenic modified N-acetylneuraminic acid substrates of the invention and the methods employing them are useful for detecting human influenza neuraminidase activity in clinical samples or specimens and for determining the type of human influenza neuraminidase present in the sample. Accordingly, these substrates and methods are useful for diagnosing influenza infection generally as well as the type of influenza infection present in the human patient from whom the clinical sample was collected. In this regard, the term "influenza" is intended to include influenza types A and B and parainfluenza types 1, 2, 3, and 4. The term "selectively detect" is intended to include the ability to detect NA activity of influenza virus as compared to the activity of other types of influenza virus as well as to the activity of other types of neuraminidases of non-influenza origin (i.e., bacterial, mammalian, and the like).

The clinical samples that are tested in the invention will typically be pharyngeal, nasopharyngeal or respiratory secretions collected from patients suffering from influenza as wash, swab, or expectorate specimens. The wash, expectorate, or swab will preferably be combined with an aqueous buffer solution containing a stabilizer prior to mixing with the substrate. The buffer solution contains a buffer that maintains the pH at about 4 to 7, preferably 5.5 to 6.5, optionally about 0.1% to 10% by weight nonionic detergent, a small amount (1–20 mM) of alkaline earth metal cation (Ca, Mg, preferably Ca), and a sufficient amount of a stabilizer selected from the group consisting of alditols, monosaccharides, and disaccharides to enhance the thermal stability of the NA in the sample. The volume of buffer solution combined with the specimen will normally be 0.1 to 2 ml.

The buffer may be organic or inorganic. Examples of suitable buffers are conventional buffers of organic acids and salts thereof such as citrate buffers (e.g., monosodium citrate-disodium citrate mixture, citric acid-trisodium citrate mixture, citric acid-monosodium citrate mixture, etc.), acetate buffers (e.g., acetic acid-sodium acetate mixture), succinate buffers (e.g., succinic acid-monosodium succinate mixture, succinic acid-sodium hydroxide mixture, succinic acid-disodium succinate mixture, etc.), tartrate buffers (e.g., tartaric acid-tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumararate mixture, monosodium fumarate acid-disodium fumararate mixture), gluconate buffers (e.g., gluconic acid-sodium gluconate mixture, gluconic acid-sodium hydroxide mixture, gluconic acid-potassium gluconate mixture, etc.) oxalate buffers (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate-mixture, etc.), acetate buffers (e.g., acetic acid-sodium acetate mixture, acetic acid-sodium hydroxide mixture, etc.), malate buffers (e.g., D,L-malic acid-disodium malate mixture), phosphate buffers (e.g., monosodium phosphate-disodium phosphate mixture, monosodium phosphate-sodium hydroxide mixture, trisodium phosphate-hydrochloric acid mixture, etc.), 2-(N-morpholino) ethanesulfonic acid, [bis-(2-hydroxyethyl)imino]tris (hydroxymethyl)methane, N-2-acetamidoiminodiacetic acid, 1,3-bis[tris(hydroxymethyl)methylamino]propane, piperazine-N,N'-2-ethanesulfonic acid), N-2-acetamido-2-aminoethanesulfonic acid, 3-(N-morpholino)-2-hydroxypropanesulfonic acid, 3-(N-morpholino) propanesulfonic acid, 2-[tris(hydroxymethyl)methylamino] ethanesulfonic acid, N-2-hydroxy-ethylpiperazine-NN'-2-ethanesulfonic acid, 3-[tris-(hydroxymethyl)methylamino]-2-hydroxypropanesulfonic acid.

Examples of non-ionic detergents useful in the buffer solution are the Pluronics, for example, Polysorbate 20 or Polysorbate 80, Triton X-100, NP-40, and alkyl glucosides such as $C_8$ and $C_9$ alkyl glucosides. The detergent is an optional component and facilitates release of the NA from the viral envelope. Examples of the stabilizers that are used in the buffer solution are trihydric or higher alditols, such as glycerin, erythritol, arabitol, xylitol, sorbitol, mannitol, the hexoses glucose and fructose and the disaccharide sucrose. These stabilizers can be used alone or in combination. In order to stabilize the activity of the neuraminidase-containing viruses, the stabilizers are added to the liquid formulation/excipient system in an amount from 0.2M to 2.1M and preferably, 0.6M to 2.0M. Once mixed with the buffer solution, the sample may be stored for prolonged periods, preferably at 2° C. to 8° C., without significant loss of NA activity.

The substrate that is combined with the buffered, stabilized specimen is a chromogenic Neu5Ac derivative that is modified in the 4 position by removal of the hydroxyl group at that position, by replacement of the hydroxyl group with fluorine, or by replacement of the hydrogen of the hydroxyl group with a lower alkyl group. These substrates may be represented by the following chemical formula:

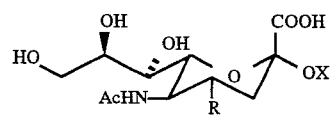

where R, X, and Ac are as defined previously. Preferably X represents 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, nitrophenylazophenyl, nitrophenylazoresorcinyl, 3-methoxyphenyl, 3-dimethylaminophenyl, 4-chloro-1-naphthyl, or 6-bromo-2-naphthyl. Simple salts of these substrates, such as the $Na^+$, $K^+$, and $NH_4^+$ salts, may also be used.

As used herein the term "chromogen" is intended to include, without limitation, molecules that exhibit absorbance or fluorescence. The term "color" is likewise intended to include, without limitation, absorbance and fluorescence.

Examples of 4-modified chromogenic Neu5Ac derivatives falling within the above formula are 4-methylumbelliferyl-4-deoxy-N-acetylneuraminic acid-alpha-ketoside, 3-cyanoumbelliferyl-4-deoxy-N-acetylneuraminic acid-alpha ketoside, 2-nitrophenyl-4-deoxy-N-acetylneuraminic acid-alpha-ketoside, 4-nitrophenyl-4-deoxy-N-acetylneuraminic acid-alpha-ketoside, 3-resorufin-4-deoxy-N-acetylneuraminic acid-alpha-ketoside, 5-bromo-4-chloro-3-indolyl-4-deoxy-N-acetylneuraminic acid-alpha-ketoside, 5-bromo-3-indolyl-4-deoxy-N-acetylneuraminic acid-alpha-ketoside, 3-indolyl-4-deoxy-N-acetylneuraminic acid-alpha-ketoside, 2-[4-(4-nitrophenylazo)-phenyl]-4-deoxy-N-acetylneuraminic acid-alpha ketoside, 2-[4(4-nitrophenylazo)resorcinyl]-4-deoxy-N-acetyl-neuraminic acid-alpha-ketoside, 3-methoxyphenyl-4-deoxy-N-acetyl-neuraminic acid-alpha-ketoside, 3-dimethylaminophenyl-4-deoxy-N-acetylneuraminic acid-alpha ketoside, 4-chloro-1-naphthyl-4-deoxy-N-acetylneuraminic acid-alpha-ketoside, 6-bromo-2-naphthyl-4-deoxy-N-acetylneuraminic acid-alpha-ketoside, 4-methylumbelliferyl-4-methoxy-N-acetylneuraminic acid-alpha-ketoside, 2-nitrophenyl-4-methoxy-N-acetylneuraminic acid-alpha-ketoside, 4-nitrophenyl-4-methoxy-N-acetylneuraminic acid-alpha-ketoside, 3-cyanoumbelliferyl-4-methoxy-N-acetylneuraminic acid-alpha-ketoside, 3-resorufin-4-methoxy-N-acetylneuraminic acid-alpha-ketoside, 5-bromo-4-chloro-3-indolyl-4-methoxy-N-acetylneuraminic acid-alpha-ketoside, 5-bromo-3-indolyl-4-methoxy-N-acetylneuraminic acid-alpha-ketoside, 3-indolyl-4-methoxy-N-acetylneuraminic acid-alpha-ketoside, 2-[4-(4-nitrophenylazo)phenyl]-4-methoxy-N-acetyl-neuraminic acid-alpha-ketoside, 2-[4-(4-nitrophenylazo) resorcinyl]-4-methoxy-N-acetylneuraminic acid-alpha-ketoside, 3-methoxyphenyl-4-methoxy-N-acetyl-neuraminic acid-alpha-ketoside, 3-dimethylaminophenyl-4-methoxy-N-acetylneuraminic acid-alpha-ketoside, 6-bromo-2-naphthyl-4-methoxy-N-acetylneuraminic acid-alpha-ketoside, 4-chloro-1-naphthyl-4-methoxy-N-acetylneuraminic acid-alpha-ketoside, 4-methylumbelliferyl-4-ethoxy-N-acetylneuraminic acid-alpha-ketoside, 2-nitrophenyl-4-ethoxy-N-acetylneuraminic acid-alpha-ketoside, 4-nitrophenyl-4-ethoxy-N-acetylneuraminic acid-alpha-ketoside, 3-cyanoumbelliferyl-4-ethoxy-N-acetylneuraminic acid-alpha-ketoside, 3-resorufin-4-ethoxy-N-acetylneuraminic acid-alpha-ketoside, 5-bromo-4-chloro-3-indolyl-4-ethoxy-N- acetylneuraminic acid-alpha-ketoside, 5-bromo-3-indolyl-4-ethoxy-N-acetylneuraminic acid-alpha-ketoside, 3-indolyl-4-ethoxy-N-acetylneuraminic acid-alpha-ketoside, 2-[4-(4-nitrophenylazo)phenyl]-4-ethoxy-N-acetyl-neuraminic acid-alpha-ketoside, 2-[4-(4-nitrophenylazo)resorcinyl]-4-ethoxy-N-acetylneuraminic acid-alpha-ketoside, 3-methoxyphenyl-4-ethoxy-N-acetyl-neuraminic acid-alpha-ketoside, 3-dimethylaminophenyl-4-ethoxy-N-acetylneuraminic acid-alpha-ketoside, 6-bromo-2-naphthyl-4-ethoxy-N-acetylneuraminic acid-alpha-ketoside, 4-chloro-1-naphthyl-4-ethoxy-N-acetylneuraminic acid-alpha-ketoside, 4-methylumbelliferyl-4-fluoro-N-acetylneuraminic acid-alpha-ketoside, 2-nitrophenyl-4-fluoro-N-acetylneuraminic acid-alpha-ketoside, 4-nitrophenyl-4-fluoro-N-acetylneuraminic acid-alpha-ketoside, 3-cyanoumbelliferyl-4-fluoro-N-acetylneuraminic acid-alpha-ketoside, 3-resorufin-4-methoxy-N-acetylneuraminic acid-alpha-ketoside, 5-bromo-4-chloro-3-indolyl-4-fluoro-N-acetylneuraminic acid-alpha-ketoside, 5-bromo-3-indolyl-4-fluoro-N-acetylneuraminic acid-alpha-ketoside, 3-indolyl-4-fluoro-N-acetylneuraminic acid-alpha-ketoside, 2-[4-(4-nitrophenylazo)phenyl]-4-fluoro-N-acetylneuraminic acid-alpha-ketoside, 2-[4-(4-nitrophenylazo)resorcinyl]-4-fluoro-N-acetylneuraminic acid-alpha-ketoside, 3-methoxyphenyl-4-fluoro-N-acetylneuraminic acid-alpha-ketoside, 3-dimethylaminophenyl-4-fluoro-N-acetylneuraminic acid-alpha-ketoside, 4-chloro-1-naphthyl-4-fluoro-N-acetylneuraminic acid-alpha-ketoside, and 6-bromo-2-naphthyl-4-fluoro-N-acetylneuraminic acid-alpha-ketosides.

The above-described Neu5Ac derivatives are generally made by protecting the functional groups of Neu5Ac at the 1, 2, 7, 8, and 9 positions, modifying the 4 position as indicated, deprotecting the 1, 2, 7, 8 and 9 positions, and coupling the 4-modified Neu5Ac with the chromogen. Details of these reactions are provided in the Examples below. More recently an improved and preferred synthesis for 4-methoxy Neu5Ac and 4-ethoxy Neu5Ac has been reported in copending U.S. patent application Ser. No. 08/286,573, filed Aug. 5, 1994, which application is hereby incorporated by reference.

The substrate will normally be added to the buffered, stabilized sample in amounts ranging between 0.05 mM and 0.5 mM. The mixture is incubated at ambient temperature to physiological temperature (i.e., about 22° C. to 37° C.) for a time sufficient to permit any NA in the sample to react with the substrate. That time will normally be in the range of 10 to 120 minutes, more usually 30 to 60 minutes. If there is NA activity in the sample, the chromogenic group will be cleaved from the substrate and the liberated chromogen will impart a characteristic color to the mixture. Since the substrates of the invention may exhibit different reactivity to the different human influenza NAs, the specific type of influenza infection maybe determined by comparing the color of the sample mixture with the color of standard reaction mixtures for each influenza NA type. For instance, influenza A may be distinguished from influenza B on the basis of substrate reactivity with the NAs of these influenza viruses. The following table indicates the color generated when NA reacts with a modified Neu5Ac and releases the chromogen.

| Released Chromogen | Type of Detection | Color |
|---|---|---|
| 5-bromo-4-chloro-3-indolol | colorimetric/visual | blue/purple in the presence of nitroblue tetrazolium |
| 5-bromo-3-indolol | colorimetric/visual | blue/purple in the presence of nitroblue tetrazolium |
| 3-indolol | colorimetric/visual | blue/purple in the presence of nitroblue tetrazolium |
| 4-methylumbelliferone | fluorometric | fluorescent emission at 45 nm after excitation at 360 nm |
| 3-cyanoumbelliferone | fluorometric | fluorescent emission at 454 nm after excitation at 415 nm |
| resorufin | colorimetric/visual | pink/red |
| 2-nitrophenol | colorimetric/visual | yellow |
| 4-nitrophenol | colorimetric/visual | yellow |
| nitrophenylazophenol | colorimetric/visual | orange |
| nitrophenylazoresorcinol | colorimetric/visual | green blue (presence of $Mg^{++}$) |
| 3-methoxyphenol | colorimetric visual | red to blue after reaction with diazonium salt |
| 3-dimethylaminophenol | colorimetric visual | red to blue after reaction with diazonium salt |
| 4-chloro-1-naphthol | colorimetric/visual | red to blue after reaction with diazonium salt |
| 6-bromo-2-naphthol | colorimetric/visual | red to blue after reaction with diazonium salt |

Accordingly, the present invention provides a simple and rapid technique for selectively diagnosing influenza that may be carried out in the clinic or physician's office and enable the physician to prescribe the appropriate therapy to treat the infection and/or the appropriate prophylactic treatment to persons in close contact with the infected patient.

The invention is further illustrated by the following examples. These examples are not intended to limit the invention in any manner.

EXAMPLE 1

Synthesis of 4-Deoxy Neu5Ac

The reaction scheme for this synthesis is shown in FIG. 1. Neu5Ac (500 mg) in 100 ml of methanol and 1.25 g of Dowex-50W ($H^+$) are heated under reflux for 20 hours, and treated with decolorizing carbon to afford the methyl ester methyl ketoside of Neu5Ac (Neu5Ac-MEMK). To the ketoside in dry acetone (dried over molecular sieves) is added catalytic p-toluenesulfonic acid monohydrate and the reaction allowed to stir for 4 hours at room temperature (RT). Neutralization with Dowex-1 (acetate form) and solvent evaporation gives 8,9-isopropylidene Neu5Ac methyl ester methyl ketoside. The 4-mesylate-8,9-isopropylidene Neu5Ac methyl ester methyl ketoside is obtained by treatment of the acetal with methanesulfonyl-chlorine in methylene chloride and 1.5 equivalents of triethylamine at 0° C. for 30 min. The mesylate is then treated with sodium iodide in acetone or methyl ethyl ketone and heated to ca. 100° C. in a sealed reaction vial to form the 4-iodo compound. Subsequent hydrogenation over palladium on carbon affords the 4-deoxy molecule. Deprotection is accomplished by treatment first with sodium hydroxide followed by treatment with dilute HCl/Dowex-50W (H⁺) to give 4-deoxy-N-acetylneuraminic acid.

EXAMPLE 2

Synthesis of 2-(p-Nitrophenyl)-4-Deoxy-Neu5Ac

Figure 2:
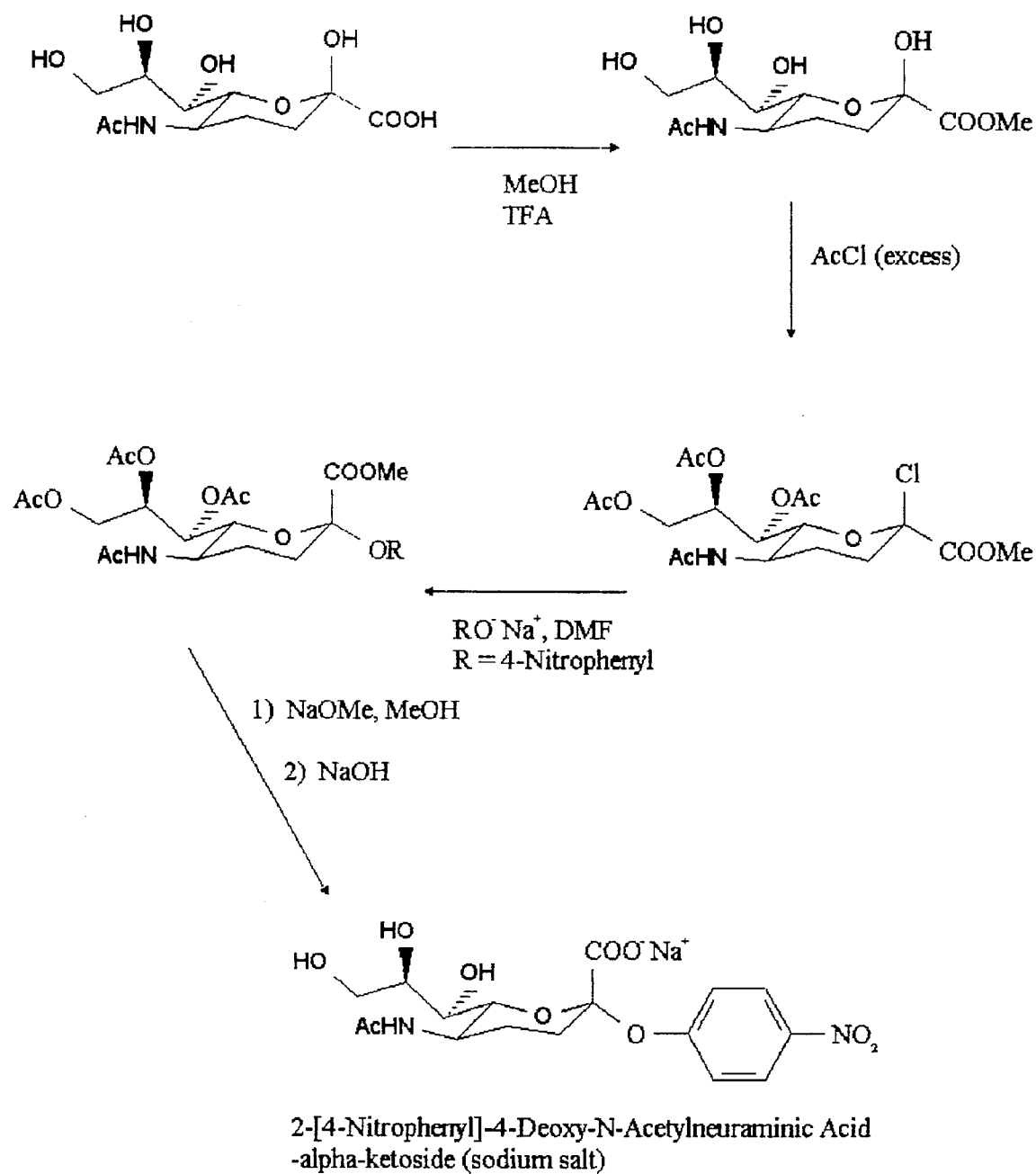

The reaction scheme for this synthesis is shown in FIG. 2. The 4-deoxy Neu5Ac of Example 1 is converted to the corresponding methyl ester by stirring at room temperature (RT) with trifluoroacetic acid in methanol. The methyl ester is then treated with an excess of acetyl chloride overnight to form the fully acetylated 2-chloro-4-deoxy Neu5Ac methyl ester. This intermediate is then treated with the sodium salt of the para-nitrophenol in dimethylformamide (DMF) at RT for 2 hours. The coupled chromogenic 4-deoxy Neu5Ac is then deprotected by treatment with sodium methoxide in methanol (1 hour) followed by treatment with sodium hydroxide (2 hours) to form the sodium salt of 2-(p-nitrophenyl)-4-deoxy-N-acetylneuraminic acid.

EXAMPLE 3

Synthesis of 4-Methoxy Neu5Ac

Figure 3:
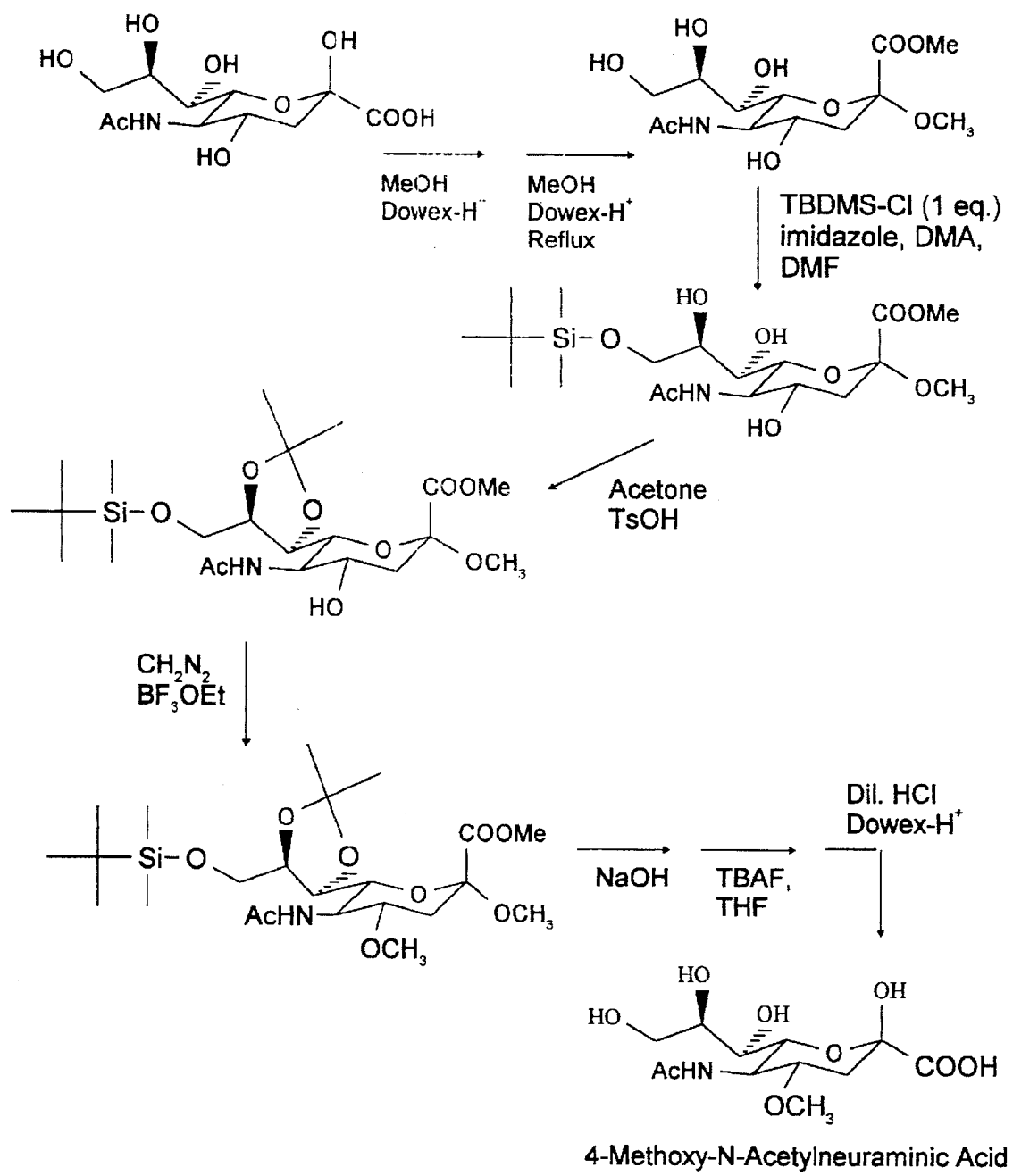

The reaction scheme for this synthesis is shown in FIG. 3. Neu5Ac-MEMK is treated with 1 eq. of tert-butyldimethylsilyl (TBDMS) chloride, imidazole and a catalytic amount of 4-dimethylaminopyridine at 65° C. to afford 9-O-TBDMS Neu5Ac-MEMK. Treatment of this compound with acetone and a catalytic amount of p-toluenesulfonic acid monohydrate at RT yields 9-O-TBDMS-7,8-isopropylidene Neu5Ac-MEMK. Treatment with diazomethane/trifluoroborate in ether at 0° C. gives the corresponding 4-methoxy derivative. This compound is fully deprotected by treatment with sodium hydroxide followed by tetrabutylammonium fluoride in THF and finally by treatment with dilute HCl/Dowex-50W (H⁺) to give 4-methoxy-N-acetylneuraminic acid.

EXAMPLE 4

Synthesis of 2-(p-Nitrophenyl)-4-Methoxy Neu5Ac

Figure 4:
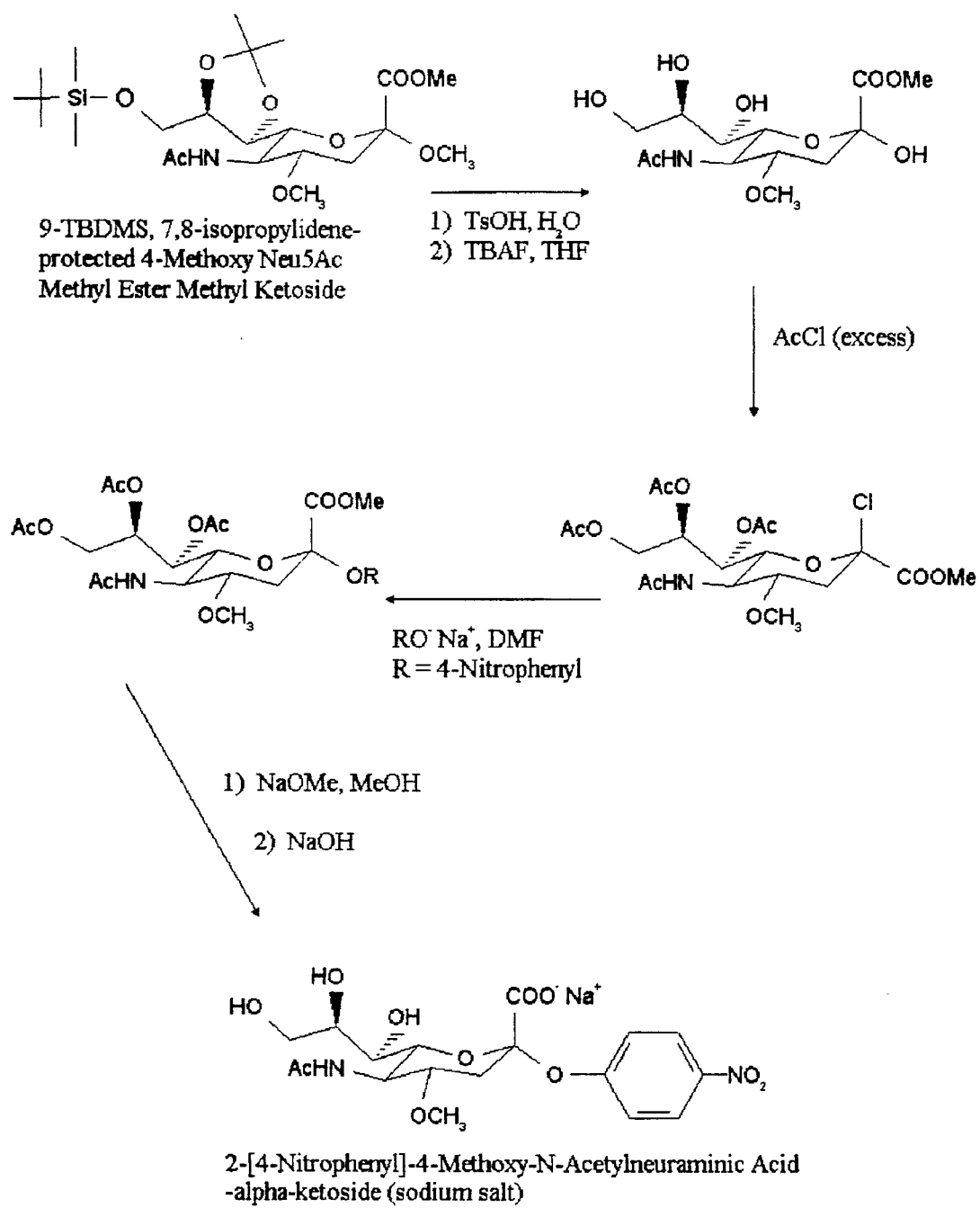

The reaction scheme for this synthesis is shown in FIG. 4. The 9-TBDMS-7,8-isopropylidene-protected 4-methoxy Neu5Ac-MEMK is deprotected with p-toluenesulfonic acid followed by tetrabutylammonium fluoride in tetrahydrofuran this intermediate is then treated with excess acetyl chloride overnight to form fully acetylated 2-chloro-4-methoxy Neu5Ac methyl ester. Coupling with the sodium salt of nitrophenol chromogen is done in dry DMF at RT for 2 hours. Deprotection and deprotonation is effected by treatment with sodium methoxide in methanol followed by treatment with sodium hydroxide to give 2-(p-nitrophenyl)-4-methoxy-N-acetylneuraminic acid, sodium salt.

EXAMPLE 5

Synthesis of 4-Fluoro Neu5Ac

Figure 5:
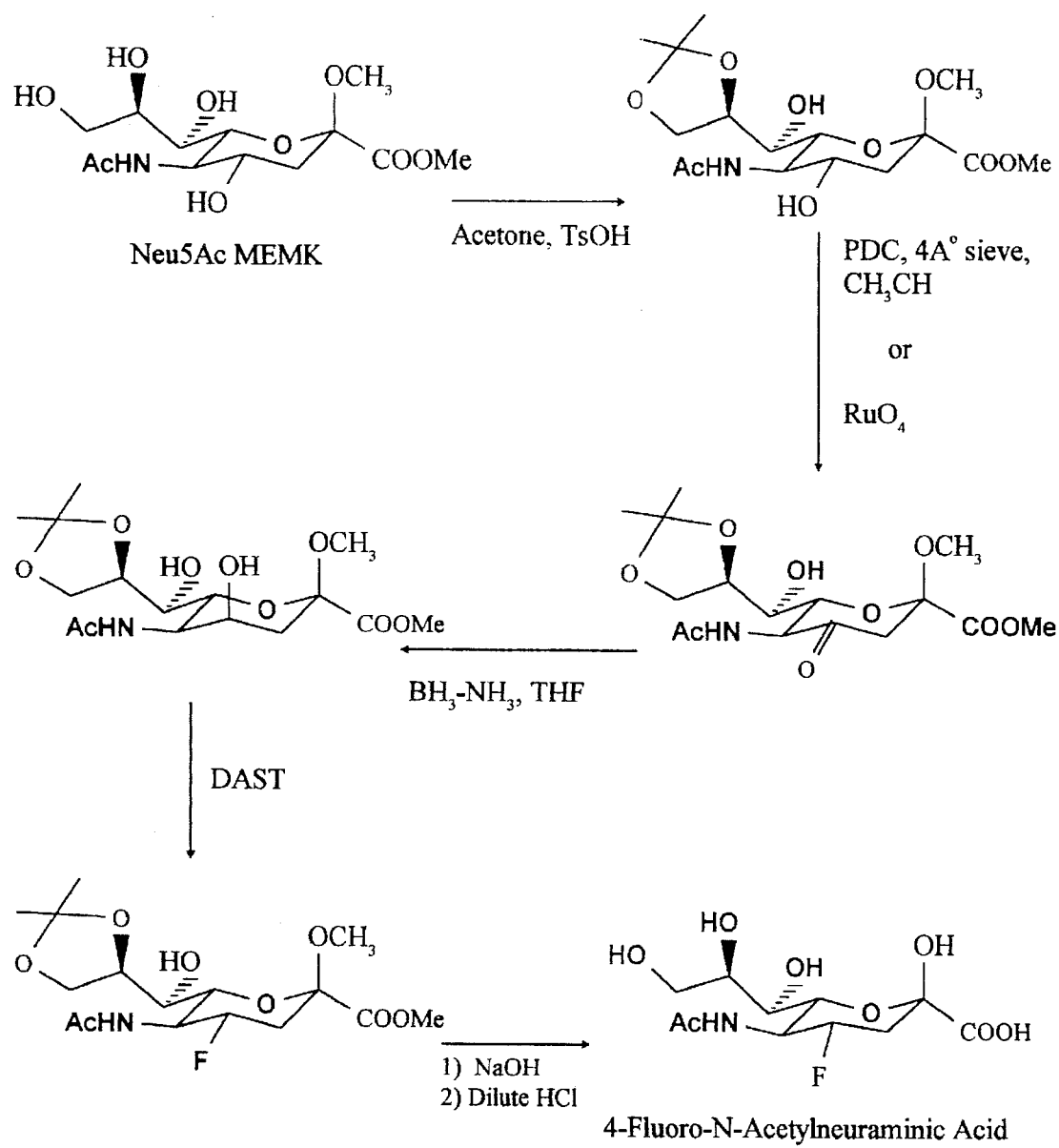

The reaction scheme for this synthesis is shown in FIG. 5. Neu5Ac (500 mg) in 100 ml of methanol and 1.25 g of Dowex-50W (H⁺) are heated under reflux for 20 hours, and treated with decolorizing carbon to afford the methyl ester methyl ketoside of Neu5Ac (Neu5Ac-MEMK). To the ketoside in dry acetone (dried over molecular sieves) is added catalytic p-toluenesulfonic acid monohydrate and the reaction allowed to stir for 4 hours at room temperature (RT). Neutralization with Dowex-1 (acetate form) and solvent evaporation gives 8, 9-isopropylidene Neu5Ac methyl ester methyl ketoside. This compound is then selectively oxidized to the 4-keto derivative with either pyridinium dichromate (PDC) or ruthenium tetra-oxide, with 4 angstrom molecular sieves in acetonitrile. Mild reduction with borane-ammonia in tetrahydrofuran affords the inverted 4-alcohol which may then be converted to the 4-fluoride (with inversion of configuration) with diethylamino sulfur trifluoride (DAST). Deprotection is accomplished by treatment first with sodium hydroxide followed by treatment with dilute HCl/Dowex-50W (H⁺) to give 4-fluoro-N-acetylneuraminic acid.

EXAMPLE 6

Synthesis of 2-(4-Chloro-1-Naphthyl)-4-Fluoro Neu5Ac

Figure 6:
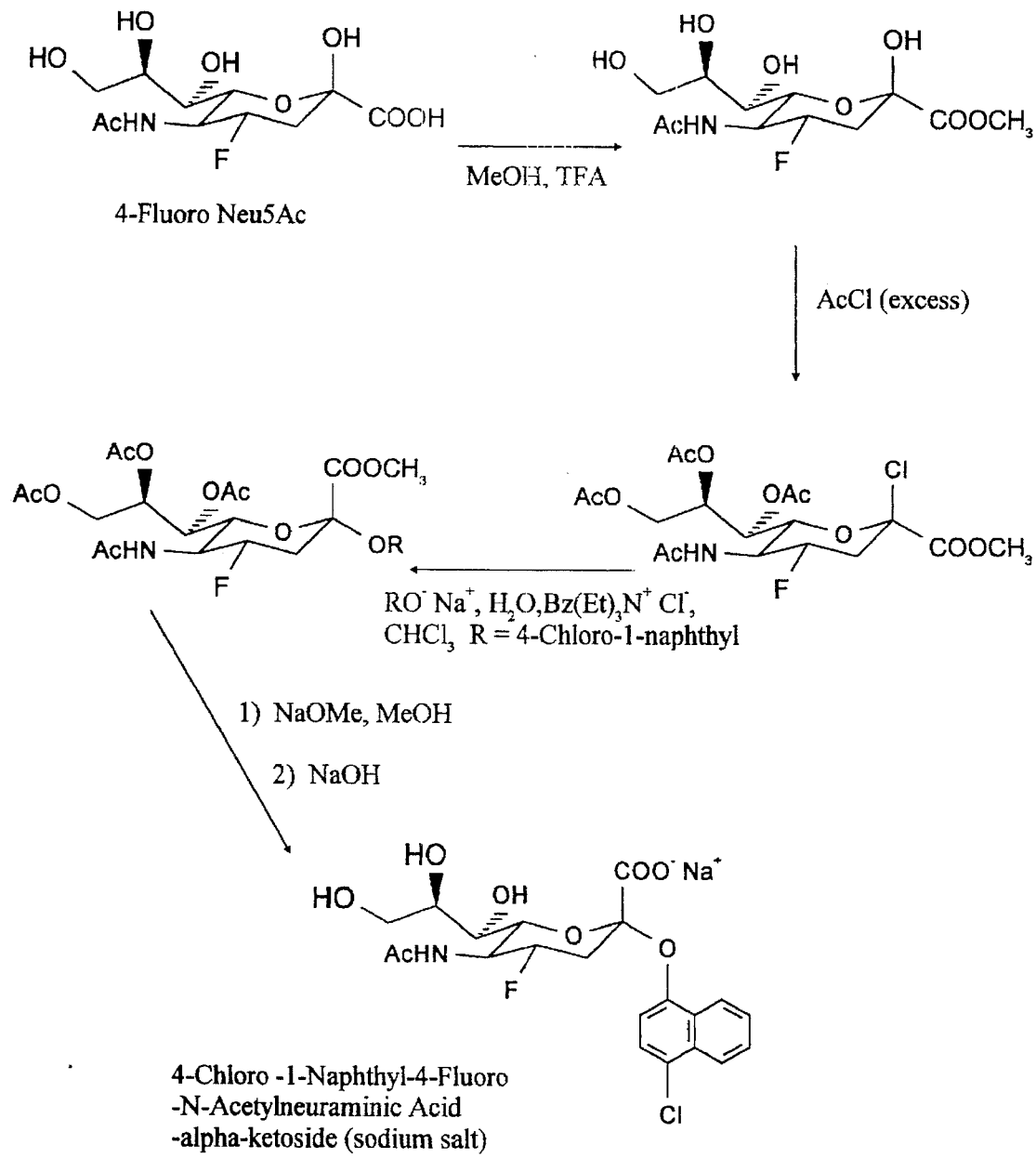

The reaction scheme for this synthesis is shown in FIG. 6. The 4-fluoro Neu5Ac of Example 5 is converted to its methyl ester by treatment in methanol with trifluoroacetic acid. Reaction in excess acetyl chloride acetylates the free alcohol groups and effects conversion to the glycosyl chloride simultaneously. The sodium salt of 4-chloro-1-naphthol (4-CN) was prepared with 1 equivalent of NaOH in water. Reaction of the glycosyl chloride in chloroform with this aqueous 4-CN solution (2.5 equivalents) in the presence of benzyl triethylammonium chloride (phase transfer reagent) affords the coupled chromogenic compound. Deprotection of the acetates and methyl ester group is accomplished by treatment with sodium methoxide and sodium hydroxide which affords the sodium salt of 2-(4-chloro-1-naphthyl)-4-fluoro Neu5Ac.

EXAMPLE 7

Enzymatic Testing of 4-Deoxy Neu5Ac

An influenza virus solution (50 µl) was mixed with a reaction mixture containing 50 µl of the substrate 4-methylumbelliferyl-Neu5Ac at various concentrations in the submillimolar to millimolar range, 150 µl of the inhibitor 4-deoxy Neu5Ac at various concentrations in the submillimolar to millimolar range, and 50 µl of 100 mM $CaCl_2$. All solutions were made up in 50 mM sodium acetate buffer, pH 5.9, to a final volume of 500 µl. After incubation at 37° C. for 15 to 30 minutes (depending on virus strain), the reaction was terminated by adding 500 µl of 1M Tris, pH 9.0 with 1.33% ethanol. The fluorescence intensity was measured at an excitation wavelength of 360 nm and an emission wavelength of 450 nm with a fluorescence spectrophotometer (Hitachi Model 3010). 4-Methyl-umbelliferone in 1M Tris, pH 9.0 with 1.33% ethanol served as a standard. Enzyme activity was expressed as mM of Neu5Ac liberated per minute per 50 µl of virus. A plot of 1/v versus 1/[S] for varying concentrations of substrate and inhibitor showed typical competitive inhibition. Plotting the slopes of the 1/v versus 1/[S] plot versus the inhibitor concentration allowed for the calculation of $K_i$ for 4-deoxy Neu5Ac as follows:

| Virus Subtype | $K_i$ (nM) |
| --- | --- |
| Influenza A (H1N1) | 0.998 |
| Influenza A (H3N2) | 2.198 |
| Influenza B | 1.050 |

(The native substrate Neu5Ac, had a $K_i$=0.626 mM when the Influenza A (H1N1) virus was used.)

The $K_i$ for 4-deoxy Neu5Ac indicates how the compound interacts with the enzyme as well as the rate at which it interacts. In general, the lower the $K_i$, the greater the degree of inhibition at any given substrate and inhibitor concentration. It is also desirable to have a modified compound which can interact with an enzyme in a similar manner as the native compound without compromising its ability as a substrate. The $K_i$ gives a first indication of the compound's interaction with the enzyme.

EXAMPLE 8

Discrimination Between Bacterial and Viral Neuraminidase

This example illustrates the ability of the present invention to discriminate between bacterial and viral infections. Such an ability is necessary and critical in the development of a useful and reliable influenza assay or test. Based on testing of both healthy and influenza-positive individuals, it has been found that a majority of individuals have an oral bacterial population which secretes bacterial neuraminidase into the oral cavity. Generally the amount of such bacterial neuraminidase is significantly higher than influenza neuraminidase in influenza-positive individuals. Thus, the presence of bacterial neuraminidase would likely result in false-positives for healthy individuals and "swamp out" viral neuraminidase in influenza-positive individuals. A useful assay for influenza must, therefore, discriminate between bacterial and viral neuraminidase. Table 1 illustrates the superior ability of the 4-position modified N-acetylneuraminic acid substrate (i.e., 4CN-40MeNeu5Ac and 4MU-40MeNeu5Ac which both have a methoxy group at the 4-position) to discriminate between bacterial and viral neuraminidase in clinical samples as compared to a non-modified N acetylneuraminic acid substrate (i.e., 4CN-Neu 5Ac which has a hydroxyl group in the 4-position). In Table 1, "4CN-Neu5Ac" is 4-chloro-1-naphthol N-acetylneuraminic acid; "4CN-40MeNeu5Ac" is 4-chloro-1-naphthol 4-methoxy-N-acetylneuraminic acid; and "4MU-40MeNeu5Ac" is 4-methylumbelliferyl 4-methoxy-N-acetylneuraminic acid. The 4CN-40MeNeu5Ac and 4CN-Neu5Ac substrates are essentially identical except for the 4-position where the former has a methoxy group and the later has a hydroxyl group; both substrates have the same attached colorimetric group (i.e., 4-chloro-1-naphthol).

TABLE 1

Comparison of 4-Modified Neu5Ac Substrates with Non-Modified Neu5Ac Substrates

| Sample | 4CN—Neu5Ac[1] | 4CN—4OMe—Neu5Ac[2] | 4MU—4OMe—Neu5Ac[3] |
|---|---|---|---|
| Blank | negative | negative | 34.6 |
| Blank/Swab | negative | negative | 40.6 |
| IA546 Virus | >3+ | 3+ | 251.7 |
| IA546 Virus/Swab | >3+ | 3+ | 328.7 |
| Vol. #1 | negative | negative | −0.9 |
| Vol. #2 | 3+ | negative | 2.6 |
| Vol. #3 | 2+ | negative | 0.3 |
| Vol. #4 | +/− | negative | 0.4 |
| Vol. #5 | negative | negative | 1.0 |
| Vol. #5 plus IA546 Virus | 3+ | 3+ | 302.2 |

[1]4-Chloro-1-naphthol-N-acetylneuraminic acid (included for comparison purposes only). Colorimetric reading are based on a scale from negative (yellow) to 3+ (deep red).
[2]4-Chloro-1-naphthol-4-methoxy-N-acetylneuraminic acid. Colorimetric reading are based on a scale from negative (yellow) to 3+ (deep red).
[3]4-Methylumbelliferyl-4-methoxy-N-acetylneuraminic acid. Blank/Swab (i.e., control) values were subtracted from experimental values.

As shown in Table 1, all substrates gave negative results with blank samples; all substrates gave positive results with known virus-containing samples (IA546 virus is a purified strain of influenza A virus). When tested with healthy individuals without any symptoms of illness (who should, therefore, test negatively for viral infection), the non-modified substrates gave both negative and positive results (i.e., false-positive) whereas the modified 4-position substrates (both colorimetric and fluorometric substrates) gave only negative results. All substrates gave positive results with a clinical sample spiked with virus, thereby indicating that the clinical samples from healthy individuals did not contain inhibiting substances. Modification of Neu5Ac at the 4-position as provided by the present invention provides the required specificity to distinguish influenza neuraminidase over bacterial neuraminidase.

Table 2 shows data obtained from the testing of supernatants from single, typed strains of oral bacteria isolated from healthy volunteers who tested positive for neuraminidase with the unmodified Neu5Ac (e.g., volunteers such as #2 and #3 in Table 1 who are not infected with influence virus). Supernatants containing high concentrations of oral bacterial neuraminidase (and no viral neuraminidase) were tested with 4MU-Neu5Ac (an unmodified N-acetylneuraminic acid substrate with a fluorometric group and a hydroxyl group at the 4-position) and 4MU-40MeNeu5Ac (a modified N-acetylneuraminic acid substrate with a fluorometric group and a methoxy group at the 4-position); the fluorometric group in each substrate is 4-methylumbelliferyl.

TABLE 2

Comparison of 4-Modified and Non-Modified N-Acetyl Neuraminic Acid Substrates in Oral Bacterial Isolates Which Produce Neuraminidase

| Supernate[1] | Dilution | 4-MU—Neu5Ac[2] | 4MU—4OMe Neu5Ac[3] |
|---|---|---|---|
| Streptococcus mitis isolate B1 | 1:2 | 408.23 | 1.01 |
| Corynebacteria Sp. isolate B2 | 1:2 | 512.60 | −4.03 |
| Streptococcus mitis isolate B3 | neat | 344.40 | 1.86 |
| Not Typed isolate B4 | neat | 394.73 | −0.83 |
| Streptococcus mitis isolate B5 | neat | 606.80 | 2.85 |
| Streptococcus mitis isolate B6 | 1:4 | 436.97 | −3.66 |
| Not typed isolate B7 | 1:4 | 544.23 | −5.18 |
| Streptococcus mitis isolate B8 | 1:4 | 519.30 | −5.34 |
| Streptococcus mitis isolate B9 | 1:2 | 469.90 | −2.58 |
| Streptococcus mitis isolate B10.1 | 1:2 | 453.10 | −2.94 |
| Streptococcus mitis isolate B10.2 | neat | 143.30 | −1.55 |

[1]Neuraminidase-producing oral bacteria were isolated from healthy volunteers, cultured for purity, and typed. Bacteria was grown in Brain Heart Infusion broth. Bacterial-free cultures were tested using fluorometric substrates. Appropriate control banks were automatically subtracted from each reading by the fluorimeter.
[2]4-Methylumbelliferyl-N-acetylneuraminic acid (included for comparison purposes only).
[3]4-Methylumbelliferyl-4-methoxy-N-acetylneuraminic acid.

In each case, assays using the unmodified substrate gave positive results whereas assays using the 4-position modified substrate gave negative results. This data demonstrates that 4-position modified Neu5Ac substrates of the present invention are not cleaved by high concentrations of oral bacterial neuraminidase. The data demonstrates the ability of the modified 4-position N-acetylneuraminic acid substrates to distinguish between bacterial and viral neuraminidase.

EXAMPLE 9

Discrimination with Naturally-Occurring Sialidase

This example illustrates the ability of the present invention to discriminate against naturally-occurring sialidase which may be present in clinical samples. Such an ability is necessary and critical in the development of a useful and reliable influenza assay or test. Naturally-occurring sialidase may be present in both healthy and influenza-positive individuals. If present at significant levels in clinical samples, such naturally-occurring sialidase can give rise to false-positive results in influenza-negative individuals in assays involving the detection of neuraminidase. A useful assay for influenza must, therefore, discriminate between naturally-occurring sialidase and viral neuraminidase. Table 3 illustrates the superior ability of the 4-position modified N-acetylneuraminic acid substrate (i.e., 4MU-4OMeNeu5Ac which has a methoxy group at the 4-position) to discriminate against naturally-occurring sialidase as compared to a non-modified N-acetylneuraminic acid substrate (i.e., 4MU-Neu5Ac which has a hydroxyl group in the 4-position). The data in Table 3 is presented graphically in FIG. 7.

Both modified and non-modified substrates at varying concentrations were tested against aqueous solutions containing a fixed level of a mammalian sialidase isolated from Chinese hamster ovary cells. Similar results are expected from naturally-occurring human sialidase. In Table 3 and FIG. 7, "4MU-Neu5Ac" is 4-methylumbelliferyl-N-acetylneuraminic acid and "4MU-4OMeNeu5Ac" is 4-methylumbelliferyl 4-methoxy-N-acetylneuraminic acid. The fluorescence intensity data in Table 3 and FIG. 7 have been corrected for background using appropriate control samples or blanks.

TABLE 3

Comparison of 4-Modified and Non-Modified N-Acetyl Neuraminic Acid Substrates for Detecting Naturally-Occurring Mammalian Sialidase (Chinese hamster ovary cell sialidase)

| Substrate Concentration (mM) | Fluorescence Intensity | |
|---|---|---|
| | 4MU—Neu5Ac | 4MU—4OMeNeu5Ac |
| 0 | 0.01 | 0.08 |
| 0.002 | 7.63 | 0.13 |
| 0.004 | 15.85 | 0.28 |
| 0.020 | 63.58 | 1.03 |
| 0.040 | 126.10 | 2.74 |
| 0.080 | 190.60 | 4.61 |
| 0.100 | 205.95 | 4.72 |
| 0.200 | 262.90 | 8.05 |
| 0.400 | 307.55 | 14.56 |
| 0.800 | 338.35 | 19.04 |
| 1.000 | 361.20 | 23.57 |

Figure 7:
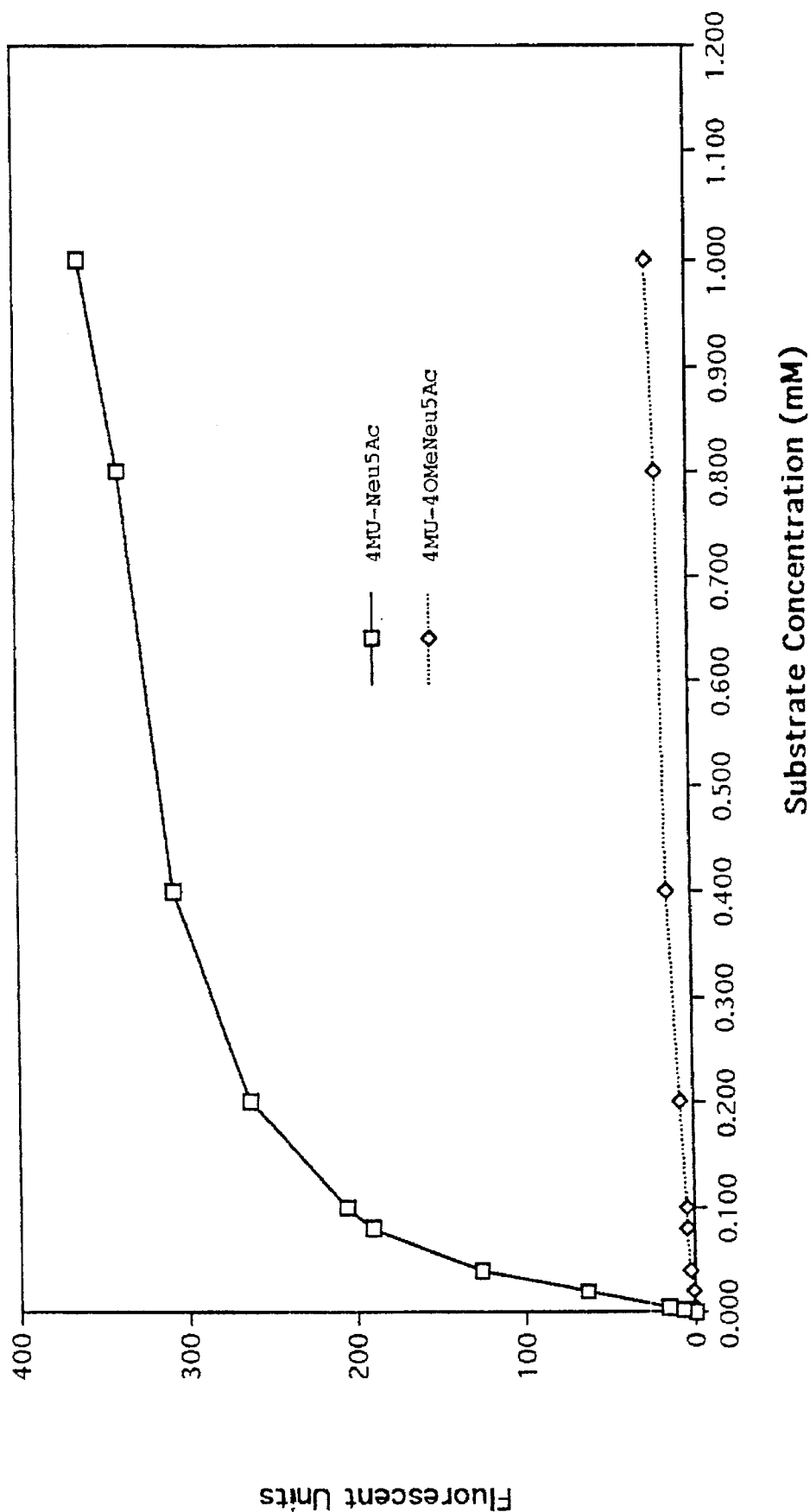

As can be seen in Table 3 and even more clearly in FIG. 7, the non-modified substrate gave significant fluorescence intensity in the presence of mammalian sialidase; such readings would likely result in significant false-positives in healthy individuals and, perhaps, alarmingly high readings in influenza-positive individuals. The modified substrate gave significantly lower readings at all levels of naturally-occurring sialidase. When compared with the fluorescence readings expected from a influenza-positive individual (see Example 8), the effect of naturally-occurring sialidase in a clinical sample tested with modified substrate would not be expected to result in false-positives for healthy individuals or to provide significantly higher or inflated results for influenza-positive individuals.

Modifications of the above-described modes for carrying out the invention that are obvious to those of skill in the fields of organic chemistry, virology, biochemistry, medical diagnostics, and related fields are intended to be within the scope of the following claims.

We claim:

1. A method of detecting human influenza neuraminidase activity in a clinical sample suspected of having such activity, said method comprising:

(a) incubating the clinical sample with a chromogenic modified N-acetylneuraminic acid substrate of the formula:

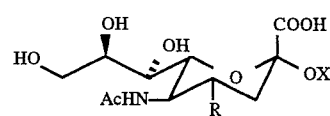

where Ac represents acetyl, R represents hydrogen, fluorine, methoxy, or ethoxy and X represents a chromogenic group that exhibits a distinct color when cleaved from the substrate or a salt of the substrate by the human influenza neuraminidase activity; and (b) detecting human influenza neuraminidase activity by observing whether the incubated clinical sample exhibits the distinct color after step (a).

2. The method of claim 1, wherein the clinical sample is a pharyngeal, nasopharyngeal, or respiratory secretion.

3. The method of claim 2, wherein R represents hydrogen and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

4. The method of claim 2, wherein R represents fluorine and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

5. The method of claim 2, wherein R represents methoxy and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

6. The method of claim 2, wherein R represents ethoxy and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

7. The method of claim 1, wherein R represents hydrogen and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

8. The method of claim 1, wherein R represents fluorine and X is selected from the group consisting of 4-methylumbelliferyl, 3-cyanoumbelliferyl, 2-nitrophenyl 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

9. The method of claim 1, wherein R represents methoxy and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

10. The method of claim 1, wherein R represents ethoxy and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

11. A method of selectively detecting human influenza neuraminidase activity in the presence of neuraminidase activity of non-influenza origin in a clinical sample suspected of having human influenza neuraminidase activity, said method comprising:

(a) incubating the clinical sample with a chromogenic modified N-acetylneuraminic acid substrate of the formula:

where Ac represents acetyl, R represents hydrogen, fluorine, methoxy, or ethoxy, and X represents a chromogenic group that exhibits a distinct color when cleaved from the substrate or a salt of the substrate by human influenza neuraminidase activity;

(b) observing the color exhibited by the incubated clinical sample after step (a); and (c) comparing the color exhibited by the incubated clinical sample to colors exhibited by standards of the human influenza neuraminidase activity and neuraminidase activity of non-influenza origin with the substrate.

12. The method of claim 11, wherein the specific type of human influenza neuraminidase activity is human influenza A neuraminidase activity, human influenza B neuraminidase activity, or parainfluenza neuraminidase activity.

13. The method of claim 12, wherein the clinical sample is a pharyngeal, nasgpharyngeal, or respiratory secretion.

14. The method of claim 12, wherein R represents hydrogen and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

15. The method of claim 12, wherein R represents fluorine and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

16. The method of claim 12, wherein R represents methoxy and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

17. The method of claim 12, wherein R represents ethoxy and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

18. The method of claim 11, wherein the clinical sample is a pharyngeal, nasopharyngeal, or respiratory secretion.

19. The method of claim 18, wherein R represents hydrogen and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

20. The method of claim 18, wherein R represents fluorine and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

21. The method of claim 18, wherein R represents methoxy and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

22. The method of claim 11, wherein R represents ethoxy and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

23. The method of claim 18, wherein R represents ethoxy and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

24. The method of claim 11, wherein R represents hydrogen and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

25. The method of claim 11, wherein R represents fluorine and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

26. The method of claim 11, wherein R represents methoxy and X is selected from the group consisting of 4-methylumbelliferyl, 3-cyanoumbelliferyl, 2-nitrophenyl, 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

27. A chromogenic substrate for detecting human influenza neuraminidase activity in a clinical sample suspected of having such activity, said substrate having the formula:

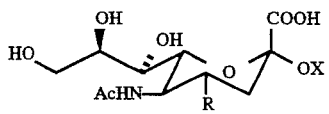

where Ac represents acetyl, R is methoxy, ethoxy, or fluorine, and X is a chromogenic group that exhibits a distinct color when cleaved from the substrate and salts of the substrate by the human influenza neuraminidase activity.

28. The chromogenic substrate of claim 27, wherein R represents methoxy and the chromogenic group is selected from the group consisting of 4-methylumbelliferyl, 3-cyanoumbelliferyl, 2- or 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

29. The chromogenic substrate of claim 27, wherein R represents ethoxy and the chromogenic group is selected from the group consisting of 4-methylumbelliferyl, 3-cyanoumbelliferyl, 2- or 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

30. The chromogenic substrate of claim 27, wherein R represents fluorine and the chromogenic group is selected from the group consisting of 4-methylumbelliferyl, 3-cyanoumbelliferyl, 2- or 4-nitrophenyl, 3-resorufin, 5-bromo-4-chloro-3-indolyl , 5-bromo-3-indolyl, 3-indolyl, 4-nitrophenylazophenyl, 4-nitrophenylazoresorcinyl, 3-methoxyphenyl, 3-dimethylaminophenyl, 4-chloro-1-naphthyl, and 6-bromo-2-naphthyl.

31. A chromogenic substrate for detecting human influenza neuraminidase activity in a clinical sample suspected of having such activity, said substrate having the formula:

where Ac represents acetyl, R is hydrogen, and X is a chromogenic group selected from the group consisting of 3-cyanoumbelliferyl, 2- or 4-nitrophenyl, 3-resorufin, 5-bromo-4-chloro-3-indolyl, 5-bromo-3-indolyl, 3-indolyl, 4-nitrophenylazophenyl, 4-nitrophenylazoresorcinyl, 3-methoxyphenyl, 3-dimethyl-aminophenyl, 4-chloro-1-naphthyl, and 6-bromo-2-naphthyl and salts of said substrate.

* * * * *